(12) United States Patent
Smiley et al.

(10) Patent No.: US 9,980,490 B1
(45) Date of Patent: May 29, 2018

(54) METHOD OF DISINFECTING BACTERIAL CONTAMINATED SURFACES OR REMOVING BACTERIA FROM CONTAMINATED SURFACES

(71) Applicant: Falcon Lab, LLC, Wilmington, DE (US)

(72) Inventors: Robert A. Smiley, Wilmington, DE (US); C. Edward Beste, Rehoboth, DE (US)

(73) Assignee: Falcon Lab, LLC, Wilmington, DE (US)

( * ) Notice: Subject to any disclaimer, the term of this patent is extended or adjusted under 35 U.S.C. 154(b) by 0 days. days.

(21) Appl. No.: 14/615,201

(22) Filed: Feb. 5, 2015

Related U.S. Application Data

(60) Provisional application No. 62/008,188, filed on Jun. 5, 2014.

(51) Int. Cl.
*A01N 37/00* (2006.01)
*A01N 59/00* (2006.01)
*A01N 37/02* (2006.01)

(52) U.S. Cl.
CPC .............. *A01N 59/00* (2013.01); *A01N 37/02* (2013.01)

(58) Field of Classification Search
CPC ...................................................... A01N 37/00
USPC .......................................................... 514/558
See application file for complete search history.

(56) References Cited

U.S. PATENT DOCUMENTS

| | | | | |
|---|---|---|---|---|
| 3,867,300 A | * | 2/1975 | Karabinos | A01N 37/02 510/132 |
| 4,404,040 A | | 9/1983 | Wang | |
| 5,330,769 A | | 7/1994 | McKinzie et al. | |
| 5,700,759 A | | 12/1997 | Caulder et al. | |
| 6,323,156 B1 | * | 11/2001 | Smiley | A01N 37/02 504/320 |
| 6,468,944 B1 | | 10/2002 | Bugg et al. | |
| 2006/0199737 A1 | * | 9/2006 | Smiley | A01N 57/20 504/165 |
| 2014/0100288 A1 | * | 4/2014 | DeSzalay | A61K 8/40 514/643 |

FOREIGN PATENT DOCUMENTS

GB    2224425    *    5/1990

OTHER PUBLICATIONS

J.V. Karabinos, H.J. Ferlin; "Bactericidal Activity of Certain Fatty Acids"; The Journal of the American Oil Chemists' Society: Jun. 1954, vol. 31, Issue 6, pp. 228-232.

J.J. Kabara; "Antimicrobial Agents Derived From Fatty Acids"; The Journal of the American Oil Chemists' Society; Feb. 1984; vol. 61, No. 2; pp. 397-403.

* cited by examiner

*Primary Examiner* — Jeffrey S Lundgren
*Assistant Examiner* — Stephanie K Springer
(74) *Attorney, Agent, or Firm* — John Wilson Jones; Jones Delflache LLP

(57) ABSTRACT

Bacterial contaminated surfaces may be disinfected or bacteria removed from a bacterial contaminated surface by applying onto the surface an anti-bactericidally effective amount of an ammonium compound represented by the formula $R_1COO^-X^+$ wherein $R_1$ is a $C_7$ to $C_{11}$ hydrocarbyl group, optionally substituted with one or more hydroxyl or $C_1$-$C_5$ hydrocarbyl groups and X is ammonium.

18 Claims, No Drawings

METHOD OF DISINFECTING BACTERIAL CONTAMINATED SURFACES OR REMOVING BACTERIA FROM CONTAMINATED SURFACES

This application claims the benefit of U.S. Patent Application Ser. No. 62/008,188, filed on Jun. 5, 2014, herein incorporated by reference.

FIELD OF THE DISCLOSURE

The disclosure relates to the use of ammonium salts of $C_7$-$C_{11}$ fatty acids for disinfecting a bacterial contaminated surface and/or the removal of bacteria from a bacterial contaminated surface.

BACKGROUND OF THE DISCLOSURE

It has become apparent in recent years that bacterial infections in hospitals, nursing homes, gyms, animal barns and other places where disease-causing bacteria can survive and spread have risen significantly. Furthermore, many strains of bacteria have become increasingly more resistant to available antibiotics that previously could be used to treat acquired infections. Thus, infections acquired in environments where bacteria thrive are and will continue to be serious health threats.

Efforts to control bacterial infection in places where such illnesses can spread, such as hospitals, are usually centered on destroying the organisms that cause infection with antimicrobial agents known as disinfectants or sanitizers.

Disinfectants, as defined by the Environmental Protection Agency (EPA), are liquid substances that can be sprayed or wiped on hard inanimate surfaces that result in the destruction or irreversible inactivation of infectious fungi and bacteria on the treated surface. Hospital disinfectants are most critical to infection control and are used on medical and dental instruments, floors and walls, bed linens, toilet seats and other surfaces.

Sanitizers are used to reduce, but not necessarily eliminate, the activity of microorganisms from inanimate surfaces to levels considered safe as determined by public health codes or regulations. Sanitizers include food contact products that are used on sites where consumable food products are placed or stored such as dishes and cooking utensils and equipment found in dairies, food processing plants and restaurants.

By late 2013, the EPA had registered about 275 active antimicrobial ingredients. The known antimicrobials can be classified into nine main categories: acids, alcohols, aldehydes, alkalis, biquanides, halogens, oxidizing agents, phenols and quaternary ammonium compounds.

Acidic disinfectants such as acetic acid, citric acid and fatty acids destroy the bonds of nucleic acids and precipitating proteins. Their effectiveness as antimicrobial agents is highly pH dependent, i.e. increased acidity enhances their effectiveness. Concentrated solutions of acids can be corrosive, cause chemical burns, and can be detrimental to the lungs and skin at high concentrations in the air. Fatty acids are less corrosive but can only be used in combination with a soap or surfactant since they are oily substances that are insoluble in water. Fatty acids also have highly offensive odors. These characteristics limit the use of acidic disinfectants.

Alcohols such as ethanol and isopropanol are broad-spectrum antimicrobial agents that damage microbes by denaturing proteins causing membrane damage and cell lysis. To be effective disinfectants, a high concentration, usually 65-90 weight percent, must be used. The activity of alcohols is limited in the presence of organic matter. Furthermore, alcohols are highly flammable, can cause damage to rubber and plastics, and can be very irritating to injured skin.

Aldehydes such as formaldehyde and glutaraldehyde are highly effective, broad-spectrum disinfectants that mainly achieve sterilization by denaturing proteins and disrupting nucleic acids. These substances are highly irritating, toxic to humans and animals on contact or inhalation and are potentially carcinogenic; therefore their use is limited.

Alkali disinfectants, such as sodium or ammonium hydroxide, work by dissolving lipids within the envelopes of the microorganism. The activity of alkali compounds is slow but can be increased by increasing the treatment temperature. Sodium hydroxide is highly caustic and protective clothing, rubber gloves and safety glasses must be used during application. Ammonium hydroxide is very odorous and the vapors can be injurious to the eyes and lungs. Alkali disinfectants are also not considered to be effective against most bacteria.

Biguanides, as represented by chlorhexidine, kill microorganisms by reacting with the negatively charged groups on cell membranes. They can only function in a limited pH range (5-7) and are easily inactivated by soaps and detergents.

Halogen compounds such as sodium hypochlorite and iodine compounds are broad-spectrum antimicrobials that are inexpensive, readily available and easy to use. They function by denaturing proteins. Sodium hypochlorite can be very caustic, is irritating to the mucous membranes, eyes and skin, is rapidly deactivated by light and some metals, loses effectiveness in the presence of other organic matter and has poor residual activity. Iodine agents have the same advantages and disadvantages as sodium hypochlorite and are deactivated by quaternary ammonium compounds and especially organic debris.

Oxidizing agents such as hydrogen peroxide and peracetic acid function by denaturing the proteins and lipids of microorganisms. In their diluted form, these agents are relatively safe but may be irritating and damage clothing when concentrated. Some metals, e.g. iron, rapidly deactivate them. They also lose effectiveness when there is organic debris present.

Phenols (pine oils) are broad-spectrum disinfectants that function by denaturing proteins and inactivating membrane-bound enzymes to alter the cell wall permeability of microorganisms. Phenols are usually applied as water emulsions with soap or detergents since they have low solubility in water. Concentrations of 5% are most effective but they are not effective against microorganism spores. Prolonged exposure to the skin may cause irritation. Concentrations over 2% are highly toxic to all animals, especially cats.

Quaternary ammonium compounds, referred to as "quats" or QACs, are cationic detergents that are attracted to negatively charged surfaces of microorganisms where they irreversibly bind phospholipids in the cell membrane and denature proteins, thus impairing permeability. They are most active at neutral to slightly alkaline pH but lose their activity at a pH less than 3.5. Organic matter, detergents, soaps and hard water readily inactivate quats.

Each of the disinfectants referenced above has serious shortcomings that limit their use. Some are hazardous to apply and none of them are effective in all situations. While most of these disinfectants have been known for decades, there have been very few antimicrobials discovered in recent years.

In J. V. Karabinos and H. J. Ferlin, *The Journal of the American Oil Chemists' Society*, June 1954, Volume 31, Issue 6, pp 228-232, the antimicrobial activity of fatty acids in the $C_9$ to $C_{12}$ range in dilute acetic acid were examined. The authors concluded that the more acidic the solution, the higher the antibacterial effectiveness. In an article entitled *Antimicrobial Agents Derived from Fatty Acids* by J. J. Kabara, *The Journal of the American Oil Chemists' Society*, vol. 61, no. 2, pp. 397-403 (1984), the author screened even numbered fatty acids from $C_8$ to $C_{18}$ (both saturated and unsaturated) for antimicrobial activity against four different bacteria. He found no activity toward *Pseudomonas aeruginiosa* while the $C_{10}$ acid (capric acid) gave the highest activity against *Streptococcus* Group A, *Staphlycoccus aureous* and *Candida albicans* of any of the fatty acids tested. The only fatty acid derivatives studied were esters.

U.S. Pat. No. 3,867,300 also discloses antimicrobial activity of fatty acids in water in the presence of non-ionic or anionic detergents at an optimal pH of 6 to 8. U.S. Pat. No. 4,404,040 describes short-chain fatty acid compositions with sanitizer solutions in the pH range of 2.0 to 5.0. U.S. Pat. No. 5,330,769 disclose the use of mixtures of nonanoic and decanoic acids ($C_9$ and $C_{10}$ fatty acids) in strong acids as sanitizers sufficient to lower the pH of the final solutions to 1 to 5. In addition to low pH, these references require water solubilizers or emulsifiers in the formulations with the fatty acids in order to allow the acids to be dispensed in water.

It should be understood that the above-described discussion is provided for illustrative purposes only and is not intended to limit the scope or subject matter of the appended claims or those of any related patent application or patent. Thus, none of the appended claims or claims of any related application or patent should be limited by the above discussion or construed to address, include or exclude each or any of the above-cited features or disadvantages merely because of the mention thereof herein.

Accordingly, there is a need for alternative disinfectants effective against microorganisms, are safe to use without protective gear (other than eye protection) during their use, are non-toxic to humans or animals by ingestion or absorption through the skin and are relatively low cost.

SUMMARY OF THE DISCLOSURE

In an embodiment of the disclosure, a method of disinfecting a bacterial contaminated surface is provided. In this embodiment, a bactericidal effective amount of an ammonium compound may be applied onto the contaminated surface. The ammonium compound may be represented by the formula $R_1COO^-X^+$ wherein $R_1$ is a $C_7$ to $C_{11}$ hydrocarbyl group, optionally substituted with one or more hydroxyl or $C_1$-$C_5$ hydrocarbyl groups and X is ammonium.

In another embodiment of the disclosure, a method of removing bacteria from a bacterial contaminated surface is provided. In this method, a bacterial effective amount of an ammonium compound is applied onto the contaminated surface. The ammonium compound is represented by the formula $R_1COO^-X^+$ wherein $R_1$ is a $C_7$ to $C_{11}$ hydrocarbyl group and X is ammonium. The $R_1$ substituent may optionally be substituted with one or more hydroxyl or $C_1$-$C_5$ hydrocarbyl groups. The ammonium compound may be applied onto one or more surfaces of vegetables.

In a preferred embodiment, the ammonium compound is ammonium pelargonate.

In another embodiment, the surface onto which the ammonium compound is applied is contaminated with a gram negative bacteria or a gram positive bacteria.

In still another embodiment, the surface onto which the ammonium compound is applied is contaminated with *Pseudomonas* aeruginiosa, *Streptococcus* Group A, *Staphlycoccus aureous*, *Staphylococcus epidermidis*, *Serratia marcescens*, *Enterococcus faecalis*, *Esherichia coli*, methicillen resistant *Staphlycoccus aureous* (MERS) or *Candida albicans* or a combination thereof.

DETAILED DESCRIPTION OF THE PREFERRED EMBODIMENTS

Characteristics and advantages of the present disclosure and additional features and benefits will be readily apparent to those skilled in the art upon consideration of the following detailed description of exemplary embodiments of the present disclosure. It should be understood that the description herein, being of example embodiments, are not intended to limit the claims of this patent or any patent or patent application claiming priority hereto. On the contrary, the intention is to cover all modifications, equivalents and alternatives falling within the spirit and scope of the claims. Many changes may be made to the particular embodiments and details disclosed herein without departing from such spirit and scope.

As used herein and throughout various portions (and headings) of this patent application, the terms "disclosure", "present disclosure" and variations thereof are not intended to mean every possible embodiment encompassed by this disclosure or any particular claim(s). Thus, the subject matter of each such reference should not be considered as necessary for, or part of, every embodiment hereof or of any particular claim(s) merely because of such reference.

Certain terms are used herein and in the appended claims to refer to particular components. As one skilled in the art will appreciate, different persons may refer to a component by different names. This document does not intend to distinguish between components that differ in only name. Also, the terms "including" and "comprising" are used herein and in the appended claims in an open-ended fashion, and thus should be interpreted to mean "including, but not limited to . . . ." Further, reference herein and in the appended claims to components and aspects in a singular tense does not necessarily limit the present disclosure or appended claims to only one such component or aspect, but should be interpreted generally to mean one or more, as may be suitable and desirable in each particular instance.

Ammonium salts (soaps) of fatty acids defined herein have been found to be highly effective, water-soluble disinfectants. They are non-flammable and have little or no odor. Furthermore, they belong to a class of substances known as hydrotropes that allows them to be used to emulsify or solubilize water insoluble compounds that heretofore have been limited in their use by their water insolubility, for example fatty acids.

The ammonium salts for use as antimicrobial agents in the methods defined here are of the formula $R_1COO^-X^+$ wherein $R_1$ is a $C_7$ to $C_{11}$ hydrocarbyl group, optionally substituted with one or more hydroxyl or $C_1$-$C_5$ hydrocarbyl groups and X is ammonium. In a preferred embodiment, $R_1$ is selected from $C_8$, $C_9$, and $C_{10}$ hydrocarbyl groups. In a most preferred embodiment, the ammonium salt is an ammonium salt of nonanoic acid or ammonium pelargonate.

The antimicrobial agents defined herein are derived from renewable sources (i.e., they satisfy governmental requirements to be designated organic).

For instance, nonanoic acid is present in fruits. For example, it is present in apples, the skin of grapes and in grape pulp. It volatilizes from leaf surfaces of many plants (washes onto soil from rain), certain flowers and the biodegradation of fats. It has been quantitatively detected in drinking water, rain water and snow as well as in air, groundwater and dust. It is a volatile component of raw beef and has been detected in fresh mussels. Ammonia in the environment is a part of the nitrogen cycle and is gaseous decomposition products of animal waste. The principal form of ammonia in the atmosphere is as $NH_3$ (a gas), not as the ammonium ion, $NH_4^+$, which is not gaseous and exists only in water. When an acid comes in contact with a base such as gaseous ammonia (or ammonium ion in water), neutralization (the reaction between an acid and a base) rapidly takes place forming the ammonium salt of nonanoic acid. Since this reaction takes place with all acids found in nature, ammonium salts such as ammonium nonanoate are ubiquitous in nature. Thus, it is naturally occurring.

Although ammonium nonanoate is widely distributed in nature, it cannot be isolated in commercial quantities from natural sources since it biodegrades within 24 hours of formation according to the EPA. Thus, it is made synthetically from readily renewable resources.

The basic raw material for the synthesis of ammonium nonanoate is oleic acid isolated from agriculturally produced edible fats and oils. Oleic acid is a substance that is exempt from EPA registration (FIFRA (25)(b)). The oleic acid content of some edible fats and oils are shown in the table below. The data is from J. A. Kent, ed., *Reigel's Handbook of Industrial Chemistry*, Ninth Edition, pg. 278, 1992.

| SOURCE | % OLEIC ACID |
| --- | --- |
| Butter fat | 20.4 |
| Canola oil | 53.8 |
| Corn oil | 24.2 |
| Olive oil | 72.5 |
| Sunflower oil | 19.5 |
| Soybean oil | 22.3 |
| Tallow (animal fat) | 36.0 |

Natural-based products such as oleic acid have been isolated from both animal and vegetable fats as raw materials. All of the oleic acid sources shown in the table above are renewable with endless worldwide supplies.

Nonanoic acid may be made using oleic acid as the only starting material. In the process, air is blown through the $C_{18}$ oleic acid resulting in a 50/50 mixture of nonanoic acid (containing some $C_8$ and $C_{10}$ acid impurities) and azelaic acid, another $C_9$ substance widely distributed in nature. The two acids are separated by distillation. There is no environmental impact from this process. The final salt (soap) product, ammonium nonanoate, is made by neutralization by mixing the oleic-derived nonanoic acid with an equal molar amount of ammonia dissolved in water until a clear one-phase solution with a pH range of 7.5 to 8.5 occurs. At this point all of the acid is converted to ammonium salt: none remains in the product. There are no by-products and no purification is required. The final concentration of ammonium nonanoate depends on the amount of water used. The highest concentration that can be made is approximately 40% since above this concentration at room temperature, insoluble salt precipitates as a solid. The 40% solution can be further diluted with water to any desired concentration effective as a bactericidal substance.

Since aqueous ammonium nonanoate is a hydrotrope capable of creating uniform stable liquid mixtures with water-insoluble organic compounds, it can be used to enhance known water-insoluble antiseptics such as phenols (pine-oil) or nonanoic (pelargonic) acid.

Ammonium nonanoate is also non-toxic to mammals and birds as determined in the registration of both nonanoic acid and ammonium nonanoate as bioherbicides by the Biochemical Division of the EPA. Since the stomach of all animals and humans is strongly acidic, the oral ingestion of ammonium nonanoate results in the immediate formation of nonanoic acid by the reaction with stomach acid. As recorded in the Federal Register, Vol. 69, No. 52, p. 12672, undiluted nonanoic acid administered orally to rats at a dose of 3,200 mg/kg body weight did not cause death of any of the rats, which indicated an $LD_{50}$ of over 3,200 mg/kg. The same reference noted that nonanoic acid administered orally to rats and mice had an $LD_{50}$ of 5,000 mg/kg for both rats and mice. For male rats, the oral $LD_{50}$ was >9,000 mg/kg. *Patty's Industrial Hygiene and Toxicology* lists an oral $LD_{50}$ for rats of 15 g/kg. for nonanoic acid. The same source describes a test in which a 12% solution of nonanoic acid produced no irritation on human skin after a 48 hr. closed patch test. When nonanoic acid was delivered at 0.46 mg/liter as an aerosol for four hours to rats, there was no mortality. Rats exposed to atmospheric concentrations of 840 mg/kg$^3$ (125 ppm) for a period of 6 hours showed no symptoms of toxicity. Thus, ammonium nonanoate has low oral, inhalation and skin toxicity in humans and animals and is safe to use as a sanitizer or disinfectant, especially at the concentrations that control microorganisms.

The fatty acid ammonium salts defined herein are especially effective in surfaces contaminated with gram negative bacteria as well as surfaces contaminated with gram positive bacteria. In an embodiment, the salts are particularly effective in disinfecting surfaces contaminated with *Pseudomonas aeruginiosa, Streptococcus* Group A, *Staphlycoccus aureous, Staphylococcus epidermidis, Serratia marcescens, Enterococcus faecalis, Esherichia coli*, methicillen resistant *Staphlycoccus aureous* (MERS) or *Candida albicans* or a combination thereof.

The fatty acid ammonium salts are also effective in destroying fungus.

Bacteria may be removed from a bacterial contaminated surface by applying onto the contaminated surface a bactericidal effective amount of an ammonium salt as disclosed herein. The fatty acid ammonium salts are particularly effective in the removal of bacteria on surface of vegetables and other crops. They are particularly effective in removing *Enterococcus faecalis* and *Esherichia coli* which present threats to vegetables, including lettuce and mushrooms. The fatty acid ammonium salts may be applied before harvesting or during harvesting.

The ammonium fatty acid(s) is typically applied to the bacterial contaminated surface in an aqueous formulation. The aqueous formulation typically contains between from about 0.5 to about 5 weight percent of the ammonium fatty acid(s). In a preferred embodiment, the aqueous formulation contains between from about 1 to about 2 weight percent of the ammonium fatty acid(s).

The pH of the formulation is usually 8 or above.

All percentages set forth in the Examples are given in terms of weight units except as may otherwise be indicated.

EXAMPLES

Example 1

To test the effectiveness of aqueous ammonium salts of $C_8$ to $C_{10}$ fatty acids as antimicrobials, 1% and 2% by weight water solutions of ammonium nonanoate were made by diluting commercially available 40% by weight aqueous ammonium nonanoate (Emery Oleochemical's "Emerion™ 7000") 1/39 and 2/38 respectively with distilled water. There were no other ingredients in these solutions except the ammonium salts and water. The salt of nonanoic acid, the $C_9$ fatty acid, was chosen to be representative of the $C_8$ to $C_{10}$ fatty acids since the commercial grade of aqueous ammonium nonanoate contains up to 4% by weight of the $C_8$ and $C_{10}$ salts.

Example 2

Suspensions of test bacteria were exposed to the 1% and 2% ammonium nonanoate solutions for specified exposure times at ambient temperature. After exposure, aliquots of the suspensions were transferred to neutralizer and assayed for survivors. Appropriate culture purity, neutralizer sterility, test population, and neutralization confirmation controls were performed. The tests showed that 1% aqueous ammonium nonanoate solution gave a 5 log reduction in the population of both *Enterococcus faecalis* (gram positive) and *Escherichia coli* (gram negative) in 1 minute. This is a reduction of live bacteria of >99.999%.

Example 3

Similar tests with 2% ammonium nonanoate against *pseudomonas aeruginosa* (gram negative) gave similar results, that is, reductions in population of >99.999% in 1 minute and >99.999% reduction in population of *Staphylococcus aureous* in 2 minutes.

Examples 2 and 3 illustrate that solutions of naturally occurring ammonium salts of $C_8$ to $C_{10}$ fatty acids are highly effective antimicrobial agents. Furthermore, they are non-toxic to humans and animals by ingestion, absorption through the skin or by breathing in vapors. The results of Example 2 and 3 are superior and unexpected since the average contact time for 5 log microbe reductions with currently known disinfectants is 10-30 minutes at various practical concentrations.

What is claimed is:

1. A method of removing bacteria from a bacterial contaminated surface, the method comprising applying onto the surface an aqueous composition having a pH from 7.5 to 8.5 and consisting of water and a bactericidal effective amount of ammonium pelargonate.

2. The method of claim 1, wherein the surface is contaminated with a gram negative bacteria or a gram positive bacteria.

3. The method of claim 1, wherein the surface is contaminated with *Pseudomonas aeruginosa*, *Streptococcus* Group A, *Staphlycoccus aureous*, *Staphylococcus epidermidis*, *Serratia marcescens*, *Enterococcus faecalis*, *Esherichia coli*, methicillen resistant *Staphlycoccus aureous* (MERS) or *Candida albicans* or a combination thereof.

4. The method of claim 1, wherein the amount of ammonium pelargonate in the aqueous composition is between from about 0.5 to about 5 weight percent.

5. The method of claim 1, wherein the bacterial contaminated surface is the surface of a vegetable.

6. A method of disinfecting a bacterial contaminated surface comprising applying onto the bacterial contaminated surface a one-phase composition containing a bactericide, the one-phase composition having a pH of 7.5 to 8.5 and consisting essentially of an aqueous composition of water and a bactericidal effective amount of an ammonium compound represented by the formula $R_1COO^-X^+$ wherein $R_1$ is a $C_7$ to $C_{11}$ hydrocarbyl group, optionally substituted with one or more hydroxyl or $C_1$-$C_5$ hydrocarbyl groups and X is ammonium wherein the amount of ammonium compound in the aqueous composition is from about 0.5 to about 5 weight percent.

7. The method of claim 4, wherein the ammonium pelargonate in the aqueous composition between from about 1 to about 2 weight percent.

8. The method of claim 6, wherein the surface is contaminated with *Pseudomonas aeruginiosa*, *Streptococcus* Group A, *Staphlycoccus aureous*, *Staphylococcus epidermidis*, *Serratia marcescens*, *Enterococcus faecalis*, *Esherichia coli*, methicillen resistant *Staphlycoccus aureous* (MERS) or *Candida albicans* or a combination thereof.

9. A method of disinfecting a bacterial contaminated surface comprising applying onto the surface a composition containing a bactericide, the composition consisting essentially of a one-phase aqueous solution containing a bactericidal effective amount of a water soluble ammonium compound represented by the formula $R_1COO^-X^+$ wherein $R_1$ is a $C_7$ to $C_{11}$ hydrocarbyl group, optionally substituted with one or more hydroxyl or $C_1$-$C_5$ hydrocarbyl groups and X is ammonium and wherein the pH of the one-phase aqueous solution is from 7.5 to 8.5.

10. The method of claim 9, wherein the surface is contaminated with a gram negative bacteria or gram positive bacteria.

11. The method of claim 9, wherein $R_1$ is selected from $C_8$, $C_9$, and $C_{10}$ hydrocarbyl groups.

12. The method of claim 9, wherein the water soluble ammonium compound is ammonium pelargonate.

13. The method of claim 9, wherein the surface is contaminated with *Pseudomonas aeruginiosa*, *Streptococcus* Group A, *Staphlycoccus aurous*, *Staphylococcus epidermidis*, *Serratia marcescens*, *Enterococcus faecalis*, *Esherichia coli*, methicillen resistant *Staphlycoccus aureus* (MERS) or *Candida albinos* or a combination thereof.

14. The method of claim 13, wherein the surface is contaminated with *Enterococcus faecalis*, *Esherichia coli* or a combination thereof.

15. The method of claim 13, wherein the surface is contaminated with *Enterococcus faecalis*, *Esherichia coli* or a combination thereof.

16. The method of claim 9, wherein the water soluble ammonium compound is applied to the bacterial contaminated surface in the one-phase aqueous solution at a concentration between from about 1 to about 2 weight percent.

17. The method of claim 9, wherein the water-soluble ammonium compound is ammonium nonanoate prepared by neutralization by mixing nonanoic acid with an equivalent molar amount of ammonia dissolved in water until a clear one-phase solution with a pH range of 7.5 to 8.5 is obtained and further wherein all of the nonanoic acid is converted to ammonium salt during the neutralization such that no nonanoic acid is in the aqueous solution applied onto the bacterial contaminated surface.

18. The method of claim 9, wherein the bacterial contaminated surface is the surface of a vegetable.

* * * * *